United States Patent [19]
Ullrich et al.

[11] Patent Number: 5,856,111
[45] Date of Patent: Jan. 5, 1999

[54] METHODS FOR IDENTIFYING MODULATORS OF INSULIN RECEPTOR PHOSPHORYLATION

[75] Inventors: Axel Ullrich, München; Edmund Hoppe, Krailling; Niels Peter Hundahl Møller, München, all of Germany

[73] Assignee: Max-Planck-Gessellschaft Zur Forderung der Wissenschaften E.V., Munich, Germany

[21] Appl. No.: 751,900

[22] Filed: Nov. 18, 1996

Related U.S. Application Data

[63] Continuation of Ser. No. 203,218, Feb. 28, 1994, abandoned.
[51] Int. Cl.$^6$ .............................. C12Q 1/00; C12N 15/52; C12N 5/10
[52] U.S. Cl. .............................. 435/7.21; 435/15; 435/21; 435/194; 435/196; 435/69.1; 435/325; 536/23.5
[58] Field of Search .................................. 435/7.21, 325, 435/21, 196, 69.1, 194, 15; 536/23.5

[56] References Cited

U.S. PATENT DOCUMENTS

| | | | |
|---|---|---|---|
| 4,761,371 | 8/1988 | Bell et al. | 435/68 |
| 5,155,031 | 10/1992 | Posner et al. | 435/184 |

FOREIGN PATENT DOCUMENTS

WO 92/01050  1/1992  WIPO.

OTHER PUBLICATIONS

Goldstein et al., Receptor, vol. 3, p. 1, 1993.
Tartare et al., 1992, "Activation of Insulin–Epidermal Growth Factor EGF Receptor Chimerae Regulates EGF Receptor Binding Affinity," *J. Cell. Biol.* 116: (3) 627–634.
Zhang et al., 1991, "Identification of Skeletal Muscle Protein–Tyrosine Phosphatases by Amplification of Conserved Complementary DNA Sequences," *Biochem. Biophys. Res. Commun.* 178: (3) 1291–1297.
Yang et al., 1993, "Cloning and Expression of PTP–Pest A Novel Human Nontransmembrane Protein Tyrosine Phosphatase," *J. Biol. Chem.* 268: (9) 6622–6628.
Matthews et al., 1992, Characterization of hematopoietic intracellular protein tyrosine phosphatases:Description of a phosphatase containing on SH2 domain and another enriched in proline–, glutamic acid–, serine–, and threonine–rich sequences, Mol. Cell. Biol. 12:2396–2405.
Gu et al., 1991, Identification, cloning, and expression of a cytosolic megakaryocyte protein–tyrosine–phosphatase with sequence homology to cytoskeletal protein 4.1, Proc. Natl. Acad. Sci. USA 88:5867–5871.
Tsai et al., 1991, Isolation and characterization of temperature–sensitive and thermostable mutants of the human receptor–like protein tyrosine phosphatase LAR, J. Biol. Chem. 266(16):10534–10543.
Krueger et al., 1990, Structural diversity and evolution of human receptor–like protein tyrosine phosphatases, EMBO J. 9:3241–3252.
Sap et al., 1990, Cloning and expression of a widely expressed receptor tyrosine phosphatase, Proc. Nat. Acad. Sci. USA 87:6112–6116.
Streuli et al., 1990, Distinct functional roles of the two intracellular phosphates like domains of the receptor–linked protein tyrosine phosphatases LCA and LAR, EMBO Journal 9:2399–2407.
Tonks et al., 1990, CD45, an integral membrane protein tyrosine phosphatase, J. Biol. Chem. 265:10674–10680.
Cool et al., 1989, CDNA isolated from a human T–cell library encodes a member of the protein–tyrosine–phosphatase family, Proc. Natl. Acad. Sci. USA 86:5257–5261.
Pallen et al., 1988, Purification of a phosphotyrosine phosphatase that dephosphorylates the epidermal growth factor receptor autophosphorylation sites, Ann N.Y. Acad. Sci. 51:299–308.
Zhang and Roth, 1992, The insulin receptor–related receptor, J. Biol. Chem. 267(26):18320–18328.
Nissley et al., 1991, Insulin–like growth factor receptors, Growth Factors 5:29–43.
Soos et al., 1986, Monoclonal antibodies reacting with multiple epitopes on the human insulin receptor, Biochem. J. 235:199–208.
Ullrich et al., 1986, Insulin–like growth factor I primary structure: comparison with insulin receptor suggests structural determinants that define functional specificity, EMBO J. 5:2503–2512.
Ullrich et al., 1985, Human insulin receptor and its relationship to the tyrosine kinase family of onccogenes, Nature 313:756–761.
den Hertog et al., 1993, Receptor protein tyrosine phosphatase α activates pp60$^{c-src}$ and is involved in neuronal differentiation, EMBO J. 12(10):3789–3798.
Fantl et al., 1993, Signalling by receptor tyrosine kinases, Ann. Rev. Biochem. 62:453–481.
Lammers et al., 1993, Differential activities of protein tyrosine phosphatases in intact cells, J. Biol. Chem. 268(30):22456–22462.
Faure et al., 1992, The dephosphorylation of insulin and epidermal growth factor receptors; role of endosome–associated phosphotyrosine phosphatase(s), J. Biol. Chem. 267(16):11215–11221.
Goldstein et al., 1992, Protein–tyrosine phosphatases and the regulation of insulin action, J. Cell Biol. 48:33–42.

(List continued on next page.)

*Primary Examiner*—Sally P. Teng
*Attorney, Agent, or Firm*—Pennie & Edmonds LLP

[57] ABSTRACT

The present invention relates to cell lines useful for the screening and identification of compounds that by modulating phosphotyrosine phosphatase activity, modulate insulin receptor type tyrosine kinase mediated signal transduction. Genetically engineered cells expressing IR in culture overcome the effect of insulin on morphology and adhesion when they are also coexpressing RPTPα or RPTPε. Such engineered cell lines may be used to screen and identify nontoxic compounds that could elicit or modulate insulin signal transduction even in the absence of insulin.

18 Claims, 5 Drawing Sheets

OTHER PUBLICATIONS

Schlessinger and Ullrich, 1992, Growth factor signaling by receptor tyrosine kinases, Neuron 9:383–391.

Zheng et al., 1992 Cell transformation and activation of pp60$^{c-src}$ by overexpression of a protein tyrosine phosphatase, Nature 359:336–339.

Sun et al., 1991, Structure of the insulin receptor substrate IRS–1 defines a unique signal transduction protein, Nature 352:73–77.

Lammers et al., 1990, Transphosphorylation as a possible mechanism for insulin and epidermal growth factor receptor activation, J. Biol. Chem. 265(28):16886–16890.

Ostergaard et al., 1989, Expression of CD45 alters phosphorylation of the lck–encoded tyrosine protein kinase in murine lymphoma T–cell lines, Proc. Natl. Acad. Sci. USA 86:8959–8963.

Mustelin et al., 1989, Rapid activation of the T–cell tyrosine protein kinase pp56lck by the CD45 phosphotyrosine phosphatase, Proc. Natl. Acad. Sci. USA 86:6302–6306.

Schlessinger et al., 1988 Signal Transduction by allosteric receptor oligomerization, Trends in Biochemical Sciences 13:443–447.

Machicao et al., 1982, Phosphorylation–dephosphorylation of purified insulin receptor from human placenta; effect of insulin, FEBS Letters 149(1):96–100.

Fantus et al., 1989, Pervanadate [Peroxide(s) of vanadate] mimics insulin action in rat adipocytes via activation of the insulin receptor tyrosine kinase, Biochem. 28:8864–8871.

Kadota et al., 1987, Stimulation of Insulin–like growth factor II receptor binding and insulin receptor kinase activity in rat adipocytes, J. Biol. Chem. 262(17):8252–8256.

Meyerovitch et al., 1987, Oral administration of vanadate normalizes blood glucose levels in streptozotocin–treated rats, J. Biol. Chem. 262(14):6658–6662.

Swarup et al., 1982, Inhibition of membrane phosphotyrosyl–protein phosphatase activity by vanadate, Biochem. Biophys. Res. Comm. 107(3):1104–1109.

Tamura et al., 1984, A novel mechanism for the insulin–like effect of vanadate on glycogen synthase in rat adipocytes, J. Biol. Chem. 259(10):6650–6658.

Walton and Dixon, 1993, Protein tyrosine phosphatases, Ann. Rev. Biochem. 62:101–120.

Pot and Dixon, 1992, A thousand and two protein tyrosine phosphatases, Biochem. Biophys. Acta. 1136:35–43.

Taylor et al., 1992, Structural framework for the protein kinase family, Ann. Rev. Cell Biol. 8:429–462.

Ullrich and Schlessinger, 1990, Signal transduction by receptors with tyrosine kinase activity, Cell 61:203–212.

Hunter, 1989, Protein–tyrosine phosphatases: The other side of the coin, Cell 58:1013–1016.

Yarden and Ullrich, 1988, Growth factor receptor tyrosine kinases, Ann. Rev. Biochem. 57:443–478.

METHODS FOR IDENTIFYING MODULATORS OF INSULIN RECEPTOR PHOSPHORYLATION

This is a continuation of application Ser. No. 08/203,218, filed Feb. 28, 1994, now abandoned.

INTRODUCTION

The present invention relates to genetically engineered cells useful for the screening and identifying of compounds that affect insulin receptor-type tyrosine kinase mediated signal transduction.

The present invention further relates to methods for screening and identifying of specific compounds, that by modulating the activity of the controlling protein phosphotyrosine phosphatases, have uses in the treatment of diabetes and other diseases.

BACKGROUND OF THE INVENTION

SIGNAL TRANSDUCTION

Cellular signal transduction is a fundamental mechanism whereby external stimuli regulate diverse cellular processes are relayed to the interior of cells. The process is generally initiated by the binding of extracellular factors (such as hormones and growth factors) to membrane receptors on the cell surface. The biochemical pathways through which signals are transmitted within cells comprise a circuitry of directly or functionally connected interactive proteins.

One of the key biochemical mechanisms of signal transduction involves the reversible phosphorylation of tyrosine residues on proteins. The phosphorylation state of a protein may affect its conformation and/or enzymic activity as well as its cellular location. The phosphorylation state of a protein is modified through the reciprocal actions of protein tyrosine kinases (PTKs) and protein phosphotyrosine phosphatases (PTPs). Generally, the level of tyrosine phosphorylation increases after the cell has been stimulated by an extracellular factor. Research has largely focussed on the protein kinases (Sefton et al., 1980, Cell 20:807–16; Heldin and Westermark, 1984, Cell 37:9–20; Yarden and Ullrich, 1988, Ann. Rev. Biochem. 57:443–78; Ullrich and Schlessinger, 1990, Cell, 61:203–12).

Protein tyrosine kinases comprise a large family of transmembrane as well as cytoplasmic enzymes with multiple functional domains (Taylor et al., 1992, Ann. Rev. Cell Biol. 8:429–62). The binding of an extracellular factor or ligand allosterically transduces the signal to the inner face of the cell membrane where the cytoplasmic portion of the receptor protein tyrosine kinase (RPTKs) initiates a cascade of molecular interactions that disseminate the signal throughout the cell and into the nucleus.

Ligand-induced activation of the kinase domain and its signalling potential are mediated by receptor dimerization. Once activated, the receptor self-phosphorylates (autophosphorylation or transphosphorylation) on specific tyrosine residues of the cytoplasmic domain. (Schlessinger, 1988, Trends Biochem. Sci. 13:443–7, Schlessinger and Ullrich, 1992, Neuron, 9:383–91, and references therein).

Like the PTKs, the protein phosphotyrosine phosphatases (PTP) comprise a family of transmembrane and cytoplasmic enzymes. (Hunter, 1989, Cell, 58:1013–16; Fischer et al., 1991, Science, 253:401–6; Saito and Streuli, 1991, Cell growth and differentiation, 2:59–65; Pot and Dixon, 1992, Biochim. Biophys. Acta, 1136:35–43). As presently understood by those in the art, in general PTKs play a triggering role in signal transduction, while PTPs guarantee that the trigger is reset thereby serving to deactivate the pathway. However, the specific functions of PTPs have not yet been defined (Walton et al., 1993, Ann. Rev. Biochem., 66:101–20).

In addition to a homologous core catalytic domain, mammalian PTPs share diverse noncatalytic sequences. While some receptor protein tyrosine phosphatases (RPTPS) contain in their extracellular portions Ig-like and/or fibronectin type III repeats (e.g., LAR, Streuli et al., 1988, J. Exp. Med. 168:1523); others have small extracellular glycosylated segments (e.g., RPTPα, Sap et al., 1990, Proc. Natl. Acad. Sci. USA, 87:6112; and RPTPε, Krueger et al., 1990, EMBO J, 9:3241). In all cases, the putative ligands have yet to be identified. Other phosphotyrosine phosphatases such as PTP1B, PTPμ, PTP1C, TC-PTP, PTPH1, RPTPκ and CD45 have been cloned and their cDNAs are described in Chernoff et al., 1990, Proc. Natl. Acad. Sci. USA, 87:2735–9; Gebbink et al., 1991, FEBS Lett. 290:123–30; Shen et al., 1991, Nature, 352:736–9; Jiang et al., 1993, Mol. Cell Biol., 13:2942–51 and; Charbonneau et al., 1988, Proc. Natl. Acad. Sci. USA, 85:7182–6 respectively.

Abnormal PTK/PTP signal transduction has been associated with a variety of diseases including psoriasis, cancer and diabetes.

THE INSULIN RECEPTOR AND DIABETES MELLITUS

The insulin receptor (IR)(Ullrich et al., Nature, 313:756–61, 1985) is the prototype for a family of RPTKs structurally defined as a heterotetrameric species of two α and two β subunits. Other members of the insulin receptor-type protein tyrosine kinase (IR-PTK) family include, for example, the receptor for insulin-like growth factor 1 (IGF-1 R, Ullrich et al., 1986, EMBO J. 5:2503–12) and insulin related receptor (IRR, Zhang et al., 1992, J. Biol. Chem. 267:18320–8) the ligand(s) for which is at present unknown.

The binding of insulin to the insulin receptor triggers a variety of metabolic and growth promoting effects. Metabolic effects include glucose transport, biosynthesis of glycogen and fats, inhibition of triglyceride breakdown, and growth promoting effects include DNA synthesis, cell division and differentiation. It is known that some of these biological effects of insulin can be mimicked by vanadium salts such as vanadates and pervanadates. However, this class of compounds appears to inhibit phosphotyrosine phosphatases generally, and are potentially toxic because they contain heavy metal (U.S. Pat. No. 5,155,031; Fantus et al., 1989, Biochem., 28:8864–71; Swarup et al., 1982, Biochem. Biophys. Res. Commun. 107:1104–9).

Diabetes mellitus is a heterogeneous primary disorder of carbohydrate metabolism with multiple etiologic factors that generally involve insulin deficiency or insulin resistance or both. Type I, or juvenile onset, or insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity but the great majority of them are both insulin deficient and insulin resistant. Insulin resistence can be due to insufficient insulin receptor expression, reduced insulin-binding affinity, or any abnormality at any step along the insulin signaling pathway (Olefsky, 1988, in "Cecil Textbook of Medicine," 18th Ed., 2:1360–81)

Overall, in the United States the prevalence of diabetes is probably between 2 and 4 per cent, with Type I comprising 7 to 10 per cent of all cases. Secondary complications of diabetes have serious clinical implications, such as amputations (primarily of toes, feet, and legs) and blindness.

Insulin is the primary mode of therapy in all patients with Type I diabetes and in many with Type II diabetes. Oral hypoglycemic agents such as sulfonylureas are effective in Type II diabetic patients but approximately 10 to 20 per cent of patients do not respond or cease to respond 12–24 months after treatment began.

Effective control of glucose level is difficult to achieve for prolonged periods even with the most meticulous mode of insulin therapy in the most motivated patients. Transplantation of the pancreas or islet cells, which normally produce insulin, continues to receive extensive study as a potential treatment. In addition, efforts towards developing newer and better external or implantable insulin-delivery devices integrated with a glucose sensor continues.

SUMMARY OF THE INVENTION

The present invention relates to cell lines useful for the screening and identification of compounds that modulate insulin receptor-type tyrosine kinase (IR-PTK) mediated signal transduction.

The invention is based, in part, on the discovery that genetically engineered cells coexpressing IR and RPTPα or RPTPε in culture are not sensitive to the effects of insulin on cell morphology and adhesion. The phenotype of the cells may be used as an indicator of insulin mediated signal transduction. The claimed cell lines of the invention are, therefore, useful in screening assays for non-toxic compounds, that by modulating phosphatase activity, modulate or prolong IR-PTK signal transduction.

In specific embodiments of the present invention detailed in the example section infra, the stable coexpression of IR and RPTPα or RPTPε in baby hamster kidney (BHK) cells, and the development of cell-based assay system for IR signal transduction are described.

DETAILED DESCRIPTION OF THE INVENTION

Figure 1A:
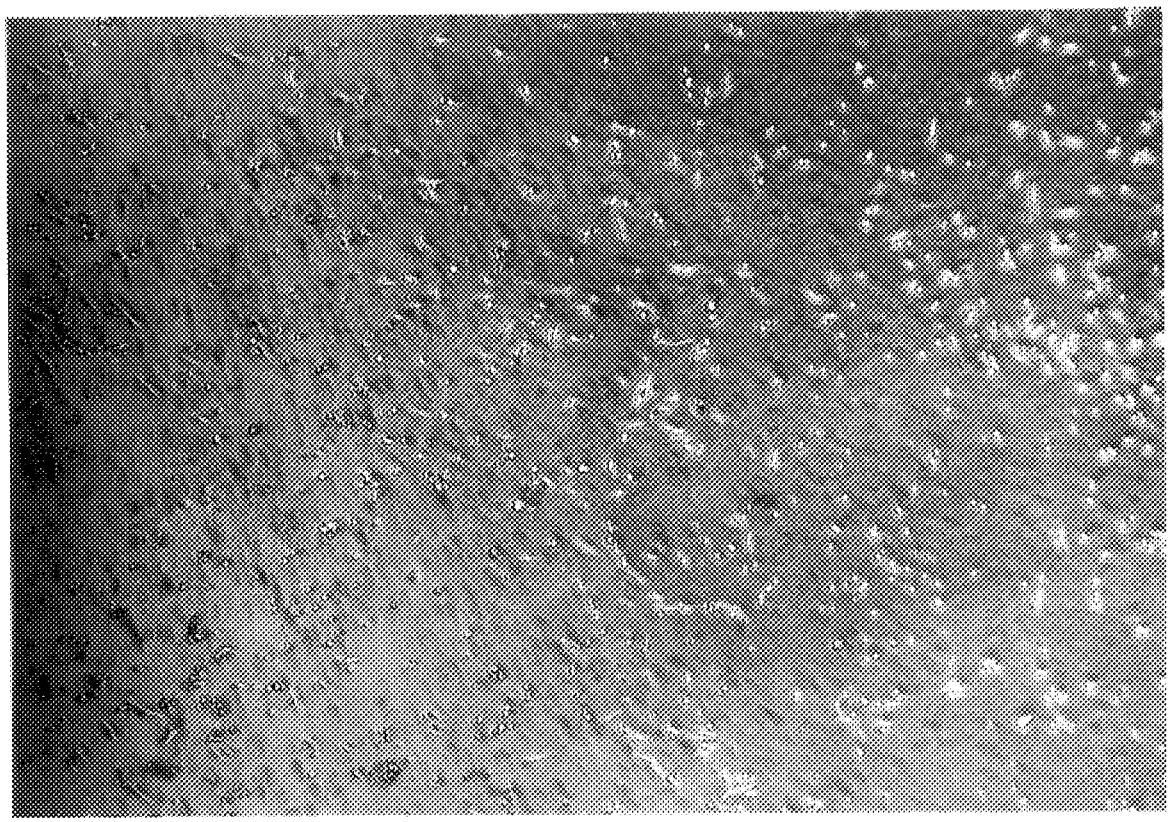
FIG. 1A is a photograph showing the insulin-induced change in phenotype of a BHK cell line expressing the insulin receptor.

The present invention is directed to cell lines useful in screening assays for compounds that modulate insulin receptor-type tyrosine kinase (IR-PTK) mediated signal transduction. The IR-PTKs include insulin receptor, insulin-like growth factor 1 (IGF-1 R) and insulin receptor related receptor (IRR). As used herein, the term signal transduction is not limited to transmembrane signalling, and includes the multiple pathways that branch off throughout the cell and into the nucleus. The term ligand is synonymous with extracellular signalling molecules, and includes insulin, IGF-1, IGF-2 and other hormones, growth factors or cytokines that may interact with IR-PTKs.

Genetically engineered cells expressing IR are sensitive to the presence of insulin in culture and this sensitivity is easily detected. More specifically, the cells respond to insulin by losing their normaly flat and adherent phenotype, and instead, round up and become detached from the culture dish. However, when these IR-expressing cells are transfected with DNA encoding RPTPα or RPTPε, the cells coexpressing IR and the phosphatase are able to grow normally in the presence of insulin. Although, the inventors do not want to be bound by any specific theoretical mechanism, it is possible that the presence of the phosphatase restores balance to the signal transduction pathways activated by the insulin receptor in the presence of its ligand.

In a preferred embodiment of the invention, genetically engineered cell lines coexpressing IR and RPTPα or RPTPε may be used to screen and identify compounds which, by modulating the activity of RPTPα or RPTPε, elicit, modulate or prolong insulin receptor signal transduction.

COEXPRESSION OF RPTPs AND IR-PTK AND GENERATION OF ENGINEERED CELL LINES

In accordance with the invention, RPTPα, RPTPε and IR nucleotide sequences or functional equivalents thereof may be used to generate recombinant DNA molecules that direct the coexpression of RPTPα or RPTPε and IR proteins or a functionaly equivalent thereof, in appropriate host cells. The nucleotide sequences of RPTPα, RPTPε and IR are reported in Sap et al., 1990, Proc. Natl. Acad. Sci. USA, 87:6112–6 and Kaplan et al., 1990, Proc. Natl. Acad. Sci. USA, 87:7000–4; Krueger et al., 1990, EMBO J, 9:3241–52; and Ullrich et al., 1985, Nature 313:756–61 respectively and are incorporated by reference herein in their entirety. The specific interaction between RPTPα, RPTPε and IR may involve the formation of a transient or stable multimolecular complex, hereinafter, referred to as RPTPα-IR, RPTPε-IR complex or generally RPTP-IR-PTK complex. As used herein, a functionaly equivalent RPTPα, RPTPε or IR refers to an enzyme with essentially the same catalytic function, but not necessarily the same catalytic activity as its native counterpart. A functionally equivalent receptor refers to a receptor which binds to its cognate ligand, but not necessarily with the same binding affinity of its counterpart native receptor.

Due to the inherent degeneracy of the genetic code, other DNA sequences which encode substantially the same or a functionally equivalent amino acid sequence, may be used in the practice of the invention for the coexpression of the RPTPα or RPTPε and IR proteins. Altered DNA sequences which may be used in accordance with the invention include deletions, additions or substitutions. For example, mutations may be introduced using techniques which are well known in the art, e.g. site directed mutagenesis, to insert new restriction sites, to alter glycosylation patterns, phosphorylation, etc. Amino acid substitutions may be made on the basis of similarity in polarity, charge, solubility, hydrophobicity, hydrophilicity, and/or the amphipatic nature of the residues involved.

The RPTPα, RPTPε or IR or a modified RPTPα, RPTPε or IR sequence may be ligated to a heterologous sequence to encode a fusion protein. For example, for screening of peptide libraries it may be useful to encode a chimeric RPTPα, RPTPε or IR protein expressing a heterologous epitope that is recognized by an antibody. A fusion protein may also be engineered to contain the ligand-binding, regulatory or catalytic domain of another PTP or PTK.

The coding sequence of RPTPα, RPTPε or IR could be synthesized in whole or in part, using chemical methods well known in the art. See, for example, Caruthers, et al., 1980, Nuc. Acids Res. Symp. Ser. 7:215–233; Crea and Horn, 180, Nucleic Acids Res. 9(10):2331; Matteucci and Caruthers, 1980, Tetrahedron Letters 21:719; and Chow and Kempe, 1981, Nucleic Acids Res. 9(12):2807–2817.

In order to coexpress a biologically active RPTPα, RPTPε or IR, the nucleotide sequence coding for RPTPα, RPTPε or IR, or their functional equivalent(s) as described supra, is inserted into one or more appropriate expression vector(s), i.e., a vector which contains the necessary elements for the transcription and translation of the inserted coding sequence (s). The RPTPα and/or RPTPε gene(s) may be placed in tandem with the IR sequence under the control of the same or different promoter used to control the expression of the other coding sequence. The two phosphatases, RPTPα and RPTPε may also be coexpressed together with IR.

Methods which are well known to those skilled in the art can be used to construct expression vectors containing the RPTPα, RPTPε and/or IR coding sequence(s) and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to coexpress the RPTPα, RPTPε, or IR coding sequences. These include but are not limited to microorganisms such as bacteria transformed with recombinant bacteriophage DNA, plasmid DNA or cosmid DNA expression vectors containing the RPTPα, RPTPε, or IR coding sequence(s) (see, Current Protocols in Molecular Biology, Vol. 2, 1988, Ed. Ausubel et al., Greene Publish. Assoc. & Wiley Interscience, Section 16.1); yeast transformed with recombinant yeast expression vectors containing the RPTPα, RPTPε, or IR coding sequence(s) (Bitner, 1987, Heterologous Gene Expression in Yeast, Methods Enzymol, Eds. Berger & Mimmel, Acad. Press, N.Y. 152:673–84); insect cell systems infected with recombinant virus expression vectors (e.g., baculovirus, see Smith et al., 1983, J. Viol. 46:584; Smith, U.S. Pat. No. 4,215,051) containing the RPTPα, RPTPεand/or IR coding sequence(s); plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the RPTPα, RPTPεand/or IR coding sequence(s) (see Weissbach & Weissbach, 1988, Methods for Plant Molecular Biology, Academic Press, NY); or animal cell systems.

In mammalian host cells, a number of viral based expression systems may be utilized. (E.g., See Logan & Shenk, 1984, Proc. Natl. Acad. Sci. (USA) 81:3655–3659, Mackett et al., 1982, Proc. Natl. Acad. Sci. (USA) 79:7415–7419; Mackett et al., 1984, J. Virol. 49:857–864).

A host cell of a particular cell type may also be chosen for the cell type-specific cofactors which may be required for the specific signalling pathway. A host cell strain may also be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, PC12 etc.

Stable expression is preferred for long-term, high-yield production of recombinant proteins in animal cells. Rather than using expression vectors which contain viral origins of replication, host cells can be transformed with RPTPα, RPTPε, or IR DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method, which is demonstrated in the examples below, may advantageously be used to engineer cell lines which stably coexpress both the RTP and IR-PTK, and which respond to ligand mediated signal transduction. Such engineered cell lines are particularly useful in screening PTP inhibitors, stimulators and analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

As the IR-PTK and RPTP may be coexpressed from different expression plasmids in the same cell, a different amplifiable selection system (for example, dhfr and adenosine deaminase) may be used for each individual plasmid. By applying different concentrations of the selecting drugs, the expression level of individual protein may be controlled separately as required (Wood et al., 1990, J. Immunol. 145:3011–16).

The host cells which contain the coding sequences and which express the biologically active gene products may be identified by at least three general approaches; (a) DNA—DNA or DNA-RNA hybridization; (b) the presence or absence of "marker" gene functions; and (c) detection of the gene products as measured by immunoassay or by their biological activity.

In the first approach, the presence of the RPTPα, RPTPε or IR coding sequence(s) inserted in the expression vector(s) can be detected by DNA—DNA or DNA-RNA hybridization using probes comprising nucleotide sequences that are homologous to the RPTPα, RPTPε or IR coding sequence (s), respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the RPTPα, RPTPε or IR coding sequence(s) is inserted within a marker gene sequence of the vector, recombinant cells containing the RPTPα, RPTPε or IR coding sequence(s) can be identified by the absence of the marker gene function. Alternatively, a marker gene can be placed in tandem with the RPTPα, RPTPε or IR sequence under the control of the same or different promoter used to control the expression of the RPTPα, RPTPε or IR coding sequence(s). Expression of the marker in response to induction or selection indicates expression of the RPTPα, RPTPε or IR coding sequence(s).

In the third approach, the expression of the RPTPα, RPTPε or IR protein product can be assessed immunologically, for example by Western blots, immunoassays such as immunoprecipitation, enzyme-linked immunoassays and the like. The ultimate test of the success of the expression system, however, involves the detection of the biologically active RPTPα, RPTPε or IR proteins. A number of assays can be used to detect activity including but not limited to ligand binding assays, phosphorylation assays, dephosphorylation assays, and biological assays using engineered cell lines as the test substrate.

The RPTPα, RPTPε or IR gene products as well as host cells or cell lines transfected or transformed with recombinant RPTPα, RPTPε and IR expression vector(s) can be used for a variety of purposes. These include but are not limited to the screening and selection of RPTPα or RPTPε analogs, or drugs that act by interacting with RTP-IR-PTK complex, or generating antibodies (i.e., monoclonal or polyclonal) that bind to the RTP-IR-PTK complex, including those that competitively inhibit the formation of such complexes. These gene products or host cells or cell lines may also be used for identifying other signalling molecules or their genes that are engaged in the insulin signalling pathway.

ASSAY SYSTEMS FOR DRUG SCREENING

In one embodiment of the invention, the RPTPs, the RPTP-IR-PTK complex, or cell lines that express the RPTPs or RPTP-IR-PTK complex, may be used to screen for molecules that modulate RPTP activity. Such molecules may include small organic or inorganic compounds, antibodies, peptides, or other molecules that modulate RPTPα's or RPTPε's dephosphorylation activity toward IR, or that promote or prevent the formation of RPTPα-IR or RPTPε-IR complex. Synthetic compounds, natural products, and other sources of potentially biologically active materials can be screened in a number of ways.

The ability of a test molecule to modulate the activity of RPTPα or RPTPε toward IR, hence signal transduction, may be measured using standard biochemical techniques, such as those described in section 6.1. Other responses such as activation or suppression of catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Ligand binding to its cellular receptor may, via signal transduction pathways, affect a variety of cellular processes. Cellular processes under the control of insulin signalling pathway may include, but are not limited to, normal cellular functions such as carbohydrate metabolism, proliferation, differentiation, maintenance of cell shape, and adhesion, in addition to abnormal or potentially deleterious processes such as apoptosis, loss of contact inhibition, blocking of differentiation or cell death. The qualitative or quantitative observation and measurement of any of the described cellular processes by techniques known in the art may be advantageously used as a means of scoring for signal transduction in the course of screening.

Described in this section are methods of the invention for screening, identification and evaluation of compounds that interact with RPTPα, RPTPε and IR and may affect various cellular processes under the control of the insulin signalling pathway.

The present invention includes a method for identifying a compound which is capable of, by modulating phosphotyrosine phosphatase activity of RPTPα and/or RPTPε, modulating insulin receptor type protein kinase IR-PTK signal transduction, comprising:

(a) contacting the compound with RPTPα and/or RPTPε and IR or, a functional derivatives thereof, in pure form, in a membrane preparation, or in a whole live or fixed cell;

(b) incubating the mixture of step (a) for an interval sufficient for the compound to stimulate or inhibit the phosphotyrosine phosphatase enzymatic activity or the signal transduction;

(c) measuring the phosphotyrosine phosphatase enzymatic activity or the signal transduction;

(d) comparing the phosphotyrosine phosphatase enzymatic activity or the signal transduction activity to that of RPTPα, and/or RPTPε and IR, incubated without the compound, thereby determining whether the compound stimulates or inhibits signal transduction.

RPTPα and/or RPTPε and IR, or functional derivatives thereof, for example, having amino acid deletions and/or insertions and/or substitutions while maintaining signal transduction, can also be used for the testing of compounds. A functional derivative may be prepared from a naturally occurring or recombinantly expressed RPTPα, RPTPε and IR by proteolytic cleavage followed by conventional purification procedures known to those skilled in the art. Alternatively, the functional derivative may be produced by recombinant DNA technology by expressing only these parts of RPTPα, RPTPε or IR in suitable cells. Cells expressing RPTPα and/or RPTPε and IR may be used as a source of RPTPα, RPTPε and/or IR, crude or purified, or in a membrane preparation, for testing in these assays. Alternatively, whole live or fixed cells may be used directly in those assays. The cells may be genetically engineered to coexpress RPTPα, RPTPε and IR. The cells may also be used as host cells for the expression of other recombinant molecules with the purpose of bringing these molecules into contact with RPTPα, RPTPε and/or IR within the cell.

IR-PTK signal transduction activity may be measured by standard biochemical techniques or by monitoring the cellular processes controlled by the signal. To assess modulation of phosphatase activity, the test molecule is added to a reaction mixture containing the phosphorylated substrate and the phosphatase. To assess modulation of kinase activity of the IR-PTK, the test molecule is added to a reaction mixture containing the IR-PTK and its substrate (in the case of autophosphorylation, the IR-PTK is also the substrate). Where the test molecule is intended to mimic ligand stimulation the assay is conducted in the absence of insulin. Where the test molecule is intended to reduce or inhibit insulin activity the presence of insulin. The kinase reaction is then initiated with the addition of ATP. An immunoassay is performed on the kinase or phosphatase reaction to detect the presence of absence of the phosphorylated tyrosine residues on the substrate, and results are compared to those obtained for controls i.e., reaction mixtures not exposed to the test molecule. The immunoassay used to detect the phosphorylated substrate in the cell lysate or the in vitro reaction mixture may be carried out with an anti-phosphotyrosine antibody. Signal transduction is mimicked if the cellular processes under the control of the signalling pathway are affected in a way similar to that caused by ligand binding. Such compounds may be naturally occurring or synthetically produced molecules that could replace the administration of insulin in the treatment of diabetes.

The invention also includes a method whereby a molecule capable of binding to RPTPα and/or RPTPε and IR in a chemical or biological preparation may be identified comprising:

(a) immobilizing RPTPα and/or RPTPε and IR, or fragments thereof, to a solid phase matrix;

(b) contacting the chemical or biological preparation with the solid phase matrix produced in step (a), for an interval sufficient to allow the compound to bind;

(c) washing away any unbound material from the solid phase matrix;

(d) detecting the presence of the compound bound to the solid phase, thereby identifying the compound.

The above method may further include the step of:

(e) eluting the bound compound from the solid phase matrix, thereby isolating the compound.

The term "compound capable of binding to RPTPα and/or RPTPε and IR" refers to a naturally occurring or synthetically produced molecule which interacts with RPTPα and/or RPTPε and IR. Such a compound may directly or indirectly modulate IR-PTK signal transduction and may include molecules that are natively associated with RPTPα, RPTPε and/or IR inside a cell. Examples of such compounds are (i) a natural substrate, of RPTPα and/or RPTPε; (ii) a naturally occurring molecule which is part of the signalling complex; iii) a natural substrate of IR-PTK, iv) a naturally occuring signalling molecule produced by other cell types.

The present invention also includes methods for identifying the specific site(s) of RPTPα, or RPTPε interaction with IR. Using the methods described herein, and biochemical and molecular biological methods well-known in the art, it is possible to identify the corresponding portions of RPTPα, RPTPε and IR involved in this interaction. For example, site-directed mutagenesis of DNA encoding either RPTPα, RPTPε or IR may be used to destroy or inhibit he interaction between the two molecules. Biophysical methods such as X-ray crystallography and nuclear magnetic resonance may also be used to map and study these sites of interaction. Once these sites have been identified, the present invention provides means for promoting or inhibiting this interaction, depending upon the desired biological outcome. Based on the foregoing, given the physical information on the sites of interaction is known, compounds that modulate catalytic activity and signal transduction may be elaborated by standard methods well known in the field of rational drug design.

The present invention further provides an assay for identifying a compound, which can block the interaction of RPTPα or RPTPε and IR. For example, a cell transfected to coexpress RPTPα or RPTPε and IR, in which the two proteins interact to form a RPTPα-IR or RPTPε-IR complex, can be incubated with an agent suspected of being able to inhibit this interaction, and the effect on the interaction measured. Any of a number of means for measuring the interaction and its disruption, such as coimmunoprecipitation, are available. The present invention also provides an assay method to identify and test a compound which stabilizes and promotes the interaction, using the same approach described above for a potential inhibitor.

Random peptide libraries consisting of all possible combinations of amino acids may be used to identify peptides that are able to bind to the substrate binding site of RPTPα or RPTPε, or other functional domains of RPTPα or RPTPε. Similarly, such libraries may also be used to identify peptides that are able to bind to the IR's site of interaction with RPTPα or RPTPε. Identification of molecules that are able to bind to RPTPα, RPTPε and IR may be accomplished by screening a peptide library with recombinant RPTPα, RPTPε or IR proteins or recombinant soluble forms of RPTPα or RPTPε or IR protein. Alternatively, the phosphatase and extracellular ligand binding domains of RPTPα or RPTPε may be separately expressed and used to screen peptide libraries.

One way to identify and isolate the peptide that interacts and forms a complex with RPTPα or RPTPε and IR, may involve labeling or "tagging" RPTPα or RPTPε and IR proteins. The RPTPα or RPTPε and IR proteins may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to RPTPα or RPTPε and IR, may be performed using techniques that are routine in the art. Alternatively, RPTPα, RPTPε or IR expression vectors may be engineered to express a chimeric RPTPα, RPTPε or IR protein containing an epitope for which a commercially available antibody exists. The epitope specific antibody may be tagged using methods well known in the art including labeling with enzymes, fluorescent dyes or colored or magnetic beads.

The present invention also includes a method for identifying and isolating a nucleic acid molecule encoding a gene product which is capable of, by modulating phosphotyrosine phosphatase activity RPTPα and/or RPTPε, modulating IR-PTK signal transduction, comprising:

(a) introducing the nucleic acid molecule into host cells coexpressing RPTPα and/or RPTPε and IR or fragments thereof;

(b) culturing the cells so that the gene product encoded by the nucleic acid molecule is expressed in the host cells and interacts with RPTPα and/or RPTPε and IR or fragments thereof;

(c) measuring the phosphotyrosine phosphatase enzymatic activity of RPTPα and/or RPTPε or IR-PTK signal transduction activity;

(d) comparing the phosphotyrosine phosphatase enzymatic activity or signal transduction to that of RPTPα and/or RPTPε and IR, or fragments thereof in cells without the nucleic acid molecule, thereby determining whether the gene product encoded by the nucleic acid molecule modulates IR-PTK signal transduction.

The above method may further include the step of:

(e) selecting and culturing the cells identified in step (d), recovering the nucleic acid molecule, thereby isolating the nucleic acid molecule.

By the term "nucleic acid molecule" is meant a naturally occurring or recombinantly generated nucleic acid molecule containing a nucleotide sequence operatively associated with an element that controls expression of the nucleotide sequence. An expression library may be created by introducing into host cells a pool of different nucleic acid molecules encoding different gene products. The host cells may be genetically engineered to coexpress RPTPα, RPTPε and IR. Such a gene library may be screened by standard biochemical techniques or by monitoring the cellular processes controlled by the signal. This approach is especially useful in identifying other native signalling molecules that are also involved in the signalling pathway.

ANTIBODY PRODUCTION AND SCREENING

Various procedures known in the art may be used for the production of antibodies to epitopes of the recombinantly produced RPTPα, RPTPε, IR, RPTPα-IR and RPTPε-IR complex. Such antibodies include but are not limited to polyclonal, monoclonal, chimeric, single chain, Fab fragments and fragments produced by an Fab expression library. Neutralizing antibodies i.e., those which compete for the substrate binding site of RPTPα or RPTPε, or the IR's site of interaction with RPTPα or RPTPε are especially preferred for therapeutics.

For the production of antibodies, various host animals may be immunized by injection with RPTPα, RPTPε, IR, RPTPα-IR or RPTPε-IR complex, or genetically engineered cells expressing RPTPα, RPTPε and IR, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to RPTPα, RPTPε, IR, RPTPα-IR and RPTPε-IR complex may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce RPTPα, RPTPε, IR, RPTPα-IR or RPTPε-IR complex-specific single chain antibodies.

Antibody fragments which contain specific binding sites of RPTPα, RPTPε, IR, RPTPα-IR or RPTPε-IR complex may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to RPTPα, RPTPε, IR, RPTPα-IR or RPTPε-IR complex.

EXAMPLE: DEMONSTRATION OF AN IN VIVO SELECTION SYSTEM FOR INSULIN RECEPTOR ACTIVATION

In the example described below, host cells were engineered to express both the IR and a series of PTPs. The cells expressing IR alone or IR plus an ineffective PTP display an altered phenotype when exposed to insulin. The results show that coexpression of RPTPα or RPTPε inhibits phosphorylation of the IR and restores normal cell phenotype. The results demonstrate that RPTP-α and RPTP-ε modulate with IR signal transduction.

MATERIAL AND METHODS

IR/BHK cells were maintained in DMEM/high glucose, 10% fetal calf serum, 10 mM glutamine, 1 μM methotrexate plus antibiotics. The cDNAs for RPTPα or RPTPε were cloned into a cytomegalovirus early promoter-based expression plasmid pCMV (Eaton et al., Biochemistry, 25:8343–47, 1986). Plasmid DNA were transfected into $10^7$ BHK cells/10 cm$^2$ plate according to the protocol of Chen and Okayama (Mol. Cell Biol., 7:2745–52, 1987). Eighteen hours after the addition of DNA precipitate, cells were washed once and supplied with fresh medium containing 0.5% serum. Forty-eight hours after transfection, the cells were split at least 1:10. Medium containing 1 μM insulin was added 12 hours later. Medium containing insulin was changed 3 times a day. Cells in culture were washed thoroughly with PBS each time the media was changed in order to remove detached cells.

The presence of insulin does not cause cell death but detachment, so it is necessary to maintain the selective pressure of insulin presence until stable co-transfected clones have grown to sufficient numbers to be isolated and characterized. This process took approximately four weeks.

Antibodies used in the analysis of protein expression and phosphorylation were the mouse monoclonal antiphosphotyrosine antibody 5E2 (Fendly et al., 1990, Cancer Res., 50:1550–8), mouse anti-IR monoclonal antibody 18–34 and rabbit antisera against the phosphatases. The rabbit antisera to RPTPα and RPTPε were prepared by standard techniques using peptide fragments derived from the C-terminus of RPTPα and RPTPε as immunogen. For detection of phosphotyrosine and protein antigens on immunoblots, the ECL system (Amersham) was used in conjunction with goat anti-mouse and anti-rabbit antibodies (Biorad). For reprobing, blots were stripped in 67 mM Tris-HCl (pH 6.8), 2% SDS, and 0.1% β-mercaptoethanol at 50° C. for 30 minutes.

SELECTION AND ANALYSIS OF CELLS BY TRANSFECTION WITH cDNAS ENCODING PTPS

The specificity of each PTP for the insulin receptor was determined by assaying insulin-induced phenotypic changes in the cells and phosphorylation of insulin receptor β-subunit by Western blot as described below.

INSULIN-INDUCED CHANGE IN PHENOTYPE

Figure 1B:
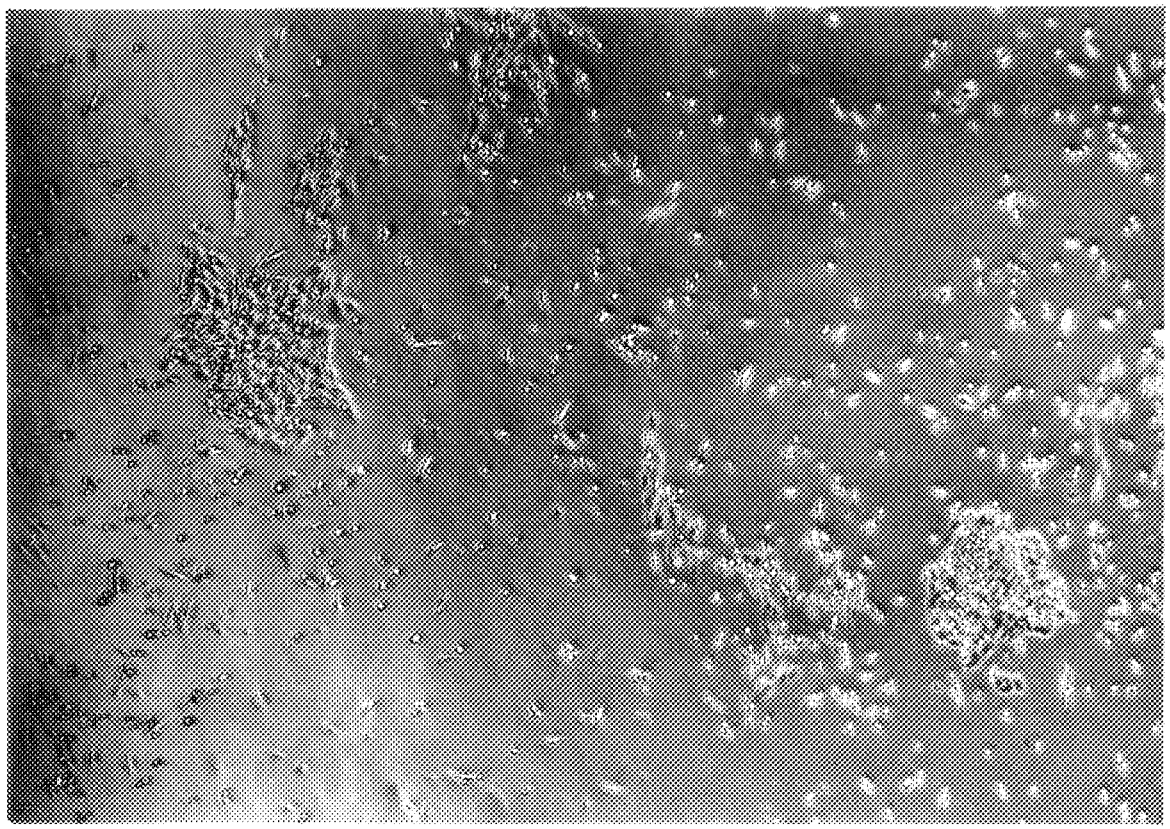
FIG. 1B is a photograph showing the phenotype of a BHK cell line coexpressing the insulin receptor and RPTPα in the presence of insulin.

In the presence of 1 μM insulin IR/BHK cells display an abnormal phenotype, i.e., rounding up and becoming detached from the plastic surface (FIG. 1A). The change in the morphology and the loss of adhesion to the substratum induced by insulin was most pronounced at low cell density and in the presence of 10% fetal calf serum. IR/BHK cells were transfected with cDNAs coding for PTP1B, PTP1BΔ299, PTP1C, PTPμ, CD45, RPTPκ, RPTPα, RPTPε, LAR, and LAR (domain 1). To determine which of these PTPs were capable of modulating IR activity thereby preventing these phenotypic changes of the cells. Only RPTPα and RPTPε, were able to restore the normal phenotype. After 24 hours of selection, small clones consisting of 4–8 cells could be seen. These transfected cells exhibited the normal phenotype and did not respond in the same manner to high doses of insulin as the cells transfected with IR alone (FIG. 1B).

AUTOPHOSPHORYLATION ASSAY BY WESTERN BLOT

Two stably cotransfected clones for each transfection (IR+RPTPα and IR+RPTPε) were starved overnight in DMEM/high glucose containing 0% fetal calf serum then stimulated with 1 μM insulin for 10 minutes. The cells were lysed and the phosphotyrosine content of insulin receptor β-subunit was detected by Western blotting (FIGS. 2 and 3) using anti-phosphotyrosine antibodies.

Figure 2A:
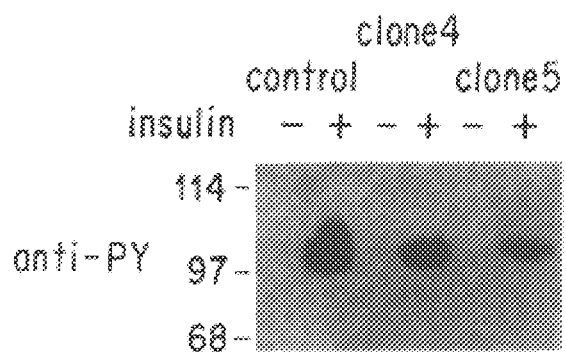
FIG. 2A shows the phosphorylation status of IR in the presence or absence of insulin in two BHK cell clones transfected with the RPTPα gene: control expressing IR alone, clones 4 and 5 coexpressing IR and RPTPα. The filter was probed with anti-phosphotyrosine (anti-PY) antibodies. The molecular weight in kD is indicated.
Figure 2B:
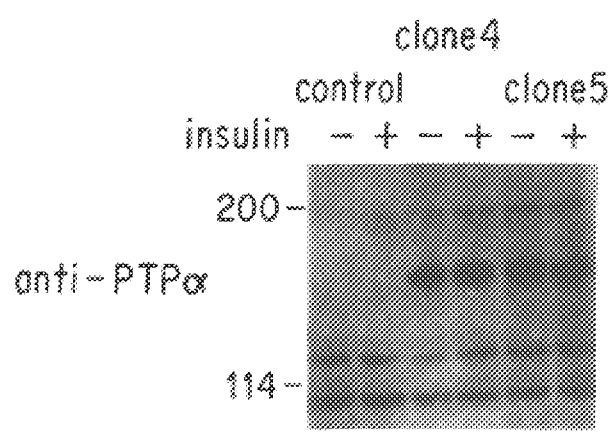
FIG. 2B shows the level of RPTPα expression in the presence or absence of insulin in BHK cell clones: control expressing IR alone, clones 4 and 5 coexpressing IR and RPTPα. The filter was probed with an anti-RPTPα antibody. The molecular weight in kD is indicated.
Figure 2C:
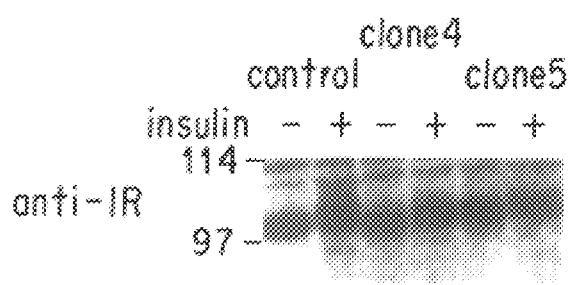
FIG. 2C shows the level of IR expression in the presence or absence of insulin in BHK cell clones: control expressing IR alone, clones 4 and 5 coexpressing IR and RPTPα. The filter was probed with an anti-IR antibody. The molecular weight in kD is indicated.

FIG. 2A shows the phosphorylation status of IR in stable BHK cell clones coexpressing IR and RPTPα. In control cells a strong tyrosine phosphorylation of insulin receptors β-subunit could be detected. This phosphorylation level was lower with the clones obtained after transfection with cDNA encoding RPTPα. FIG. 2B shows the level of RPTPα expression in the cotransfected clones. An additional band immunoreactive with anti-RPTPα antibodies, could be detected in these cotransfected clones. FIG. 2C shows the level of IR expression in control and cotransfected clones, which was similar. Stable BHK cell clone 5 coexpressing IR and RPTPα was deposited with the American Type Culture Collection, 12301 Parklawn Drive, Rockville, Md. 20852 on Jan. 20, 1994, and assigned accession number ATCC CRL 11528.

Figure 3A:
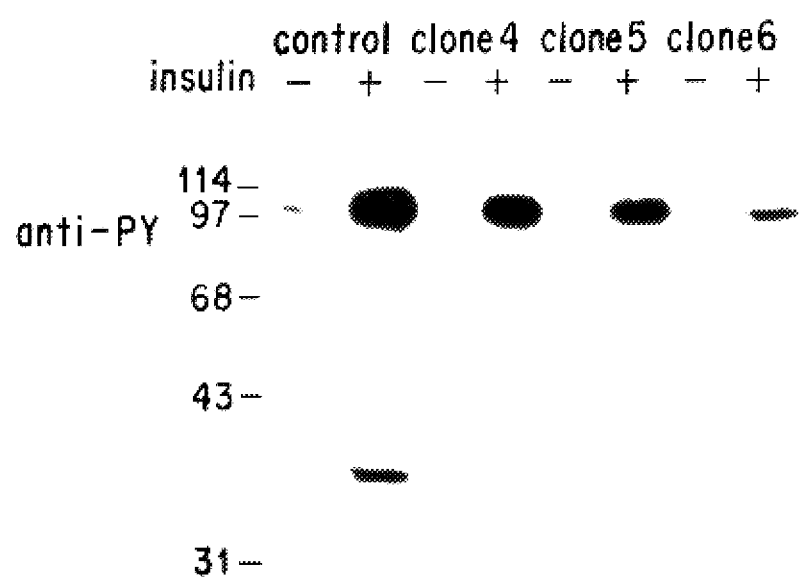
FIG. 3A shows the phosphorylation status of IR in the presence or absence of insulin in BHK cell clones: control expressing IR alone, clones 4, 5 and 6 coexpressing IR and RPTPε. The filter was probed with anti-phosphotyrosine (anti-PY) antibodies. The molecular weight in kD is indicated.
Figure 3B:
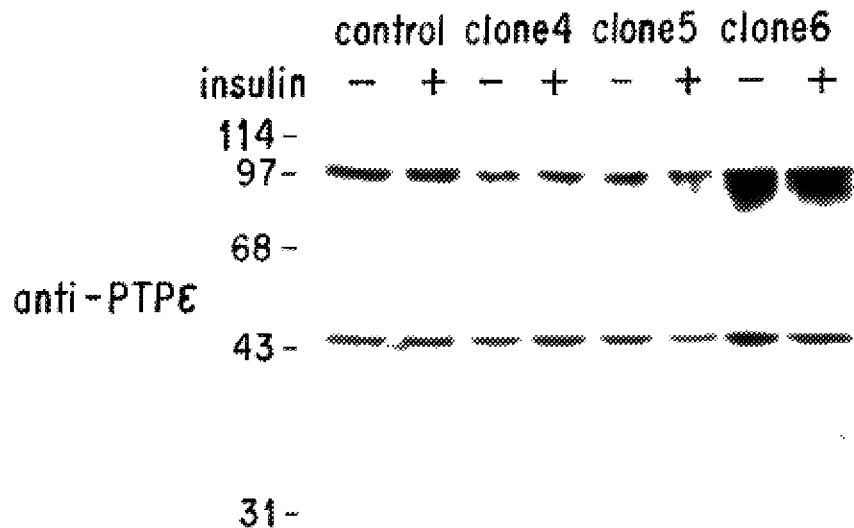
FIG. 3B shows the level of RPTPε expression in the presence or absence of insulin in BHK cell clones: control expressing IR alone, clones 4, 5 and 6 coexpressing IR and RPTPε. The filter was probed with an anti-RPTPε antibody.
Figure 3C:
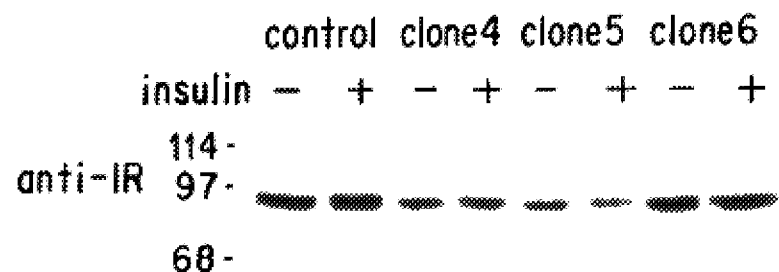
FIG. 3C shows the level of IR expression in the presence or absence of insulin in BHK cell clones: control expressing IR alone, clones 4, 5 and 6 coexpressing IR and RPTPε. The filter was probed with an anti-IR antibody. The molecular weight in kD is indicated.

As shown in FIG. 3A, 3B and 3C, the pattern of IR phosphorylation and protein expression levels in stable cell clones coexpressing IR and RPTPε are similar to that of IR and RPTPα. The data suggests that the restoration of normal phenotype of the cotransfected cells was associated with the dephosphorylation of the insulin receptor or downstream key signalling event. Stable BHK cell clone 6 coexpressing IR and RPTPε was deposited with the American Type Culture Collection, 12301 Parklawn Drive, Rockville, Md. 20852 on Jan. 20, 1994, and assigned accession number ATCC CRL 11529.

The results described clearly indicate that RPTPα and RPTPε interact specifically with IR. In the presence of insulin, RPTPα and RPTPε modulate IR signal transduction and downstream cellular processes, which prevent changes in cell morphology and adhesion properties. These cell lines could be used in a drug screen whereby any biological effect of the test compound in vivo on insulin signal transduction may be monitored by changes in the cell morphology and adhesion properties or by phosphorylation state of the insulin receptor. Drugs that interfere with RPTPα or RPTPε activity would make the cells respond to insulin and re-exhibit the insulin-sensitive phenotype.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of determining whether a compound modulates phosphorylation of a phosphorylated insulin receptor in the presence of a receptor-type phosphotyrosine phosphatase, comprising:

(a) contacting the compound with a mammalian cell in the presence of insulin, said cell cotransformed or cotransfected with DNA encoding insulin receptor and receptor-type phosphotyrosine phosphatase α or ε to coexpress insulin receptor and receptor-type phosphotyrosine phosphatase α or ε; and (b) comparing changes in the morphology of the cell in (a) with morphology of a control cell corresponding to the mammalian cell in (a) in the presence of insulin, but not exposed to the compound, wherein said change in morphology correlates with a change in the degree of phosphorylation of the insulin receptor, such that if the morphology of the cell in (a) differs from that of the control cell in (b), a compound that modulates the phosphorylation of the insulin receptor is identified.

2. The method of claim 1 wherein the morphology comprises rounding up of the cell.

3. The method of claim 1 wherein the morphology comprises detachment of the cell from a surface.

4. The method of claim 1 wherein the change in degree of phosphorylation is an increase in the degree of phosphorylation.

5. The method of claim 1 in which the insulin receptor is human insulin receptor.

6. The method of claim 5 in which the receptor-type phosphotyrosine phosphatase is human RPTPα.

7. The method of claim 6 in which the cell is a baby hamster kidney cell.

8. The method of claim 7 in which the cell is as deposited with the American Type Culture Collection and assigned accession number ATCC CRL 11528.

9. The method of claim 5 in which the receptor-type phosphotyrosine phosphatase is human RPTPε.

10. The method of claim 9 in which the cell is a baby hamster kidney cell.

11. The method of claim 10 in which the cell is as deposited with the American Type Culture Collection and assigned accession number ATCC CRL 11529.

12. A method of determining whether a compound increases phosphorylation of insulin receptor in the presence of a receptor-type phosphotyrosine phosphatase, comprising;

(a) contacting the compound with a mammalian cell attached to a surface, said cell cotransformed or cotransfected with DNA encoding insulin receptor and receptor-type phosphotyrosine phosphatase α or ε to coexpress insulin receptor and receptor-type phosphotyrosine phosphatase α or ε; and (b) comparing changes in the morphology of the cell in (a) with morphology of a control cell not exposed to the compound, wherein said morphology comprises rounding up and detachment of the cell from the surface, such that if the morphology of the cell in (a) differs from the control cell in (b), a compound that increases the phosphorylation of the insulin receptor is identified.

13. The method of claim 12 in which the insulin receptor is human insulin receptor.

14. The method of claim 12 in which the receptor-type phosphotyrosine phosphatase is human RPTPα.

15. The method of claim 12 in which the receptor-type phosphotyrosine phosphatase is human RPTPε.

16. The method of claim 12 in which the cell is a baby hamster kidney cell.

17. The method of claim 16 in which the cell is a cell as deposited with the American Type Culture Collection and assigned accession number ATCC CRL 11528.

18. The method of claim 16 in which the cell is a cell as deposited with the American Type Culture Collection and assigned accession number ATCC CRL 11529.

* * * * *